US010661086B2

(12) United States Patent
von Brasch et al.

(10) Patent No.: US 10,661,086 B2
(45) Date of Patent: May 26, 2020

(54) INDIVIDUALIZED AUDITORY PROSTHESIS FITTING (71) Applicant: Cochlear Limited, Macquarie University, NSW (AU)

(72) Inventors: Alexander von Brasch, Cremorne (AU); Stephen Fung, Dundas Valley (AU)

(73) Assignee: COCHLEAR LIMITED, Macquarie University, NSW (AU)

( * ) Notice: Subject to any disclaimer, the term of this patent is extended or adjusted under 35 U.S.C. 154(b) by 476 days.

(21) Appl. No.: 15/451,593

(22) Filed: Mar. 7, 2017

(65) Prior Publication Data
US 2018/0256895 A1 Sep. 13, 2018

(51) Int. Cl.
A61N 1/37 (2006.01)
A61N 1/372 (2006.01)
A61N 1/36 (2006.01)

(52) U.S. Cl.
CPC ..... A61N 1/37247 (2013.01); A61N 1/36039 (2017.08)

(58) Field of Classification Search
CPC .................. A61N 1/37247; A61N 1/36039
See application file for complete search history.

(56) References Cited

U.S. PATENT DOCUMENTS

| 8,548,595 | B1 | 10/2013 | Calle et al. |
| 8,996,122 | B2 | 3/2015 | Calle et al. |
| 9,247,361 | B2 | 1/2016 | Nishizaki et al. |
| 2011/0082519 | A1* | 4/2011 | Strahl ............... A61N 1/37247 607/57 |
| 2018/0160984 | A1* | 6/2018 | Mauger ............... A61B 5/7275 |

* cited by examiner

Primary Examiner — Rex R Holmes
(74) Attorney, Agent, or Firm — Edell, Shapiro & Finnan, LLC (57) ABSTRACT Embodiments of the present invention are generally directed to individualized (recipient-specific) techniques for fitting an auditory/hearing prosthesis to a recipient. In the individualized fitting techniques, a fitting system obtains data/information that is specific to the recipient to which the auditory prosthesis is being fitted. The fitting system is configured to analyze the recipient-specific data and to generate an individualized fitting plan/program that is specifically tailored to the recipient.

22 Claims, 8 Drawing Sheets

INDIVIDUALIZED AUDITORY PROSTHESIS FITTING

BACKGROUND

Field of the Invention

The present invention relates generally to fitting recipients with auditory prostheses.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to damage to the auditory nerve.

Certain individuals suffer from only partial sensorineural hearing loss and, as such, retain at least some residual hearing. These individuals may be candidates for electro-acoustic hearing prostheses.

SUMMARY

In one aspect, an apparatus for fitting an auditory prosthesis to a recipient is provided. The apparatus comprises: a display screen; one or more user input devices; and one or more processors configured to: obtain recipient-specific data associated with the recipient of the auditory prosthesis; based on the recipient-specific data, automatically generate and display an individualized fitting interface at the display screen that exposes to a user functional fitting modules that are clinically relevant for the recipient.

In another aspect, a method for fitting an auditory prosthesis to a recipient with a fitting system is provided. The method comprises: obtaining recipient-specific data associated with the recipient; analyzing the recipient-specific data to identify one or more prosthesis setting that enable the auditory prosthesis to convert sound signals into stimulation signals for delivery to the recipient; identifying selected functional fitting modules useable to determine values for the one or more prosthesis settings; and displaying the selected functional fitting modules at a display screen of the fitting system.

In another aspect, a method for fitting an auditory prosthesis to a recipient is provided. The method comprises, at an auditory prosthesis fitting system: obtaining recipient-specific data associated with the recipient; generating, based on the recipient-specific data, an individualized fitting plan to fit the auditory prosthesis to the recipient; and displaying, at a display screen of the auditory prosthesis fitting system, an indication of the individualized fitting plan for the recipient

BRIEF DESCRIPTION OF THE DRAWINGS

Embodiments of the present invention are described herein in conjunction with the accompanying drawings, in which.

DETAILED DESCRIPTION

The effectiveness of cochlear implants and other auditory prostheses generally depends on how well a particular prosthesis is configured or "fit" to the specific recipient of the auditory prosthesis. For instance, the "fitting" of an auditory prosthesis to a recipient determines configuration settings, parameters, and other data (collectively and generally referred to herein as "settings") that define the specific operational characteristics of the auditory prosthesis. Collectively, the various settings determined for a recipient during a fitting process are referred to herein as the recipient's "operational program" or "operational map" and will dictate how the auditory prosthesis operates to convert sound signals into stimulation signals for delivery to the recipient.

Depending on the nature and cause of their hearing loss, each recipient can have a different hearing perception and may require different activities during a fitting session. For example, as a recipient ages (a child becoming a teen or a young adult becoming an older adult), the fitting routine could be different as some of the settings may no longer be applicable to a recipient, while other settings may need more attention. As such, conventional clinical fitting systems and, the associated fitting software, are complicated and provide audiologists, clinicians, or other users (collectively and generally referred to herein as "clinicians") with the ability to perform a wide variety of tests/measurements and the ability to determine a large number of different types of auditory prosthesis settings. Conventional fitting techniques greatly rely on the skills (e.g., training, experience, personal knowledge, etc.) of the clinician to not only identify the specific settings that need to be determined for the recipient, but also to identify and implement a fitting process/flow that most efficiently results in the determination of the specific settings for use by the auditory prosthesis. That is, conventional fitting techniques are a "one-size-fits-all" approach that rely on the clinician to select from a large number of available options to fit an auditory prosthesis to a recipient. This heavy reliance on the clinician in conventional fitting techniques is particularly problematic as there is a shortage of trained/skilled clinicians in many geographic areas.

Embodiments of the present invention are generally directed to individualized (recipient-specific) techniques for fitting an auditory/hearing prosthesis to a recipient. The information used for the individualization of the fitting process is data that is specific to the recipient. This recipient-specific data may include, for example, the recipient's age, time since implantation, previous fitting session data, etc. In other words, the fitting process is automatically personalized for a specific recipient based on the recipient's particular characteristics/attributes. The individualized fitting techniques presented herein are designed to stream-line the fitting process, allowing the clinician to focus on only the settings, and any associated tests/measurements, that are relevant for the specific individual being fitted. This may facilitate better outcomes and lessen the reliance on the skill of the clinician to fit the recipient.

The individualized fitting techniques presented herein may be used to fit a number of different types of auditory/hearing prostheses to a recipient. However, merely for ease of illustration, the techniques presented herein are primarily described with reference to fitting one type of hearing prosthesis, namely a cochlear implant. It is to be appreciated that the techniques presented herein may be used to fit other hearing prostheses, such as auditory brainstem stimulators, electro-acoustic hearing prostheses, bimodal hearing prostheses, etc. to a recipient.

Figure 1:
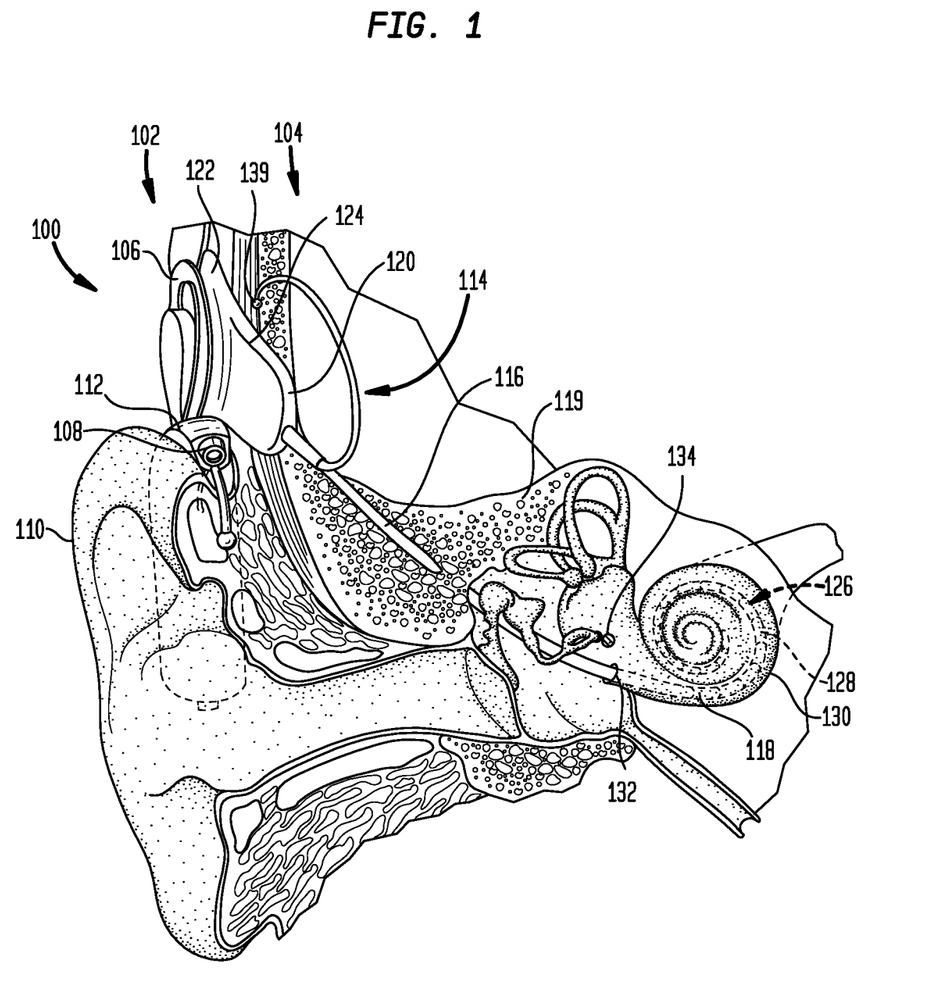
FIG. 1 is a schematic diagram illustrating a cochlear implant that may be fit to a recipient using the individualized fitting techniques presented herein.

FIG. 1 is a schematic diagram of an exemplary cochlear implant 100 that may be fit to a recipient using the individualized fitting techniques presented herein. The cochlear implant 100 comprises an external component 102 and an internal/implantable component 104.

The external component 102 is directly or indirectly attached to the body of the recipient and typically comprises an external coil 106 and, generally, a magnet (not shown in FIG. 1) fixed relative to the external coil 106. The external component 102 also comprises one or more sound input elements 108 (e.g., microphones, telecoils, etc.) for detecting/receiving input sound signals, and a sound processing unit 112. The sound processing unit 112 includes, for example, one or more batteries (not shown in FIG. 1) and a sound processor (also not shown in FIG. 1). The sound processor is configured to process electrical signals generated by a sound input element 108 that is positioned, in the depicted embodiment, by auricle 110 of the recipient. The sound processor provides the processed signals to external coil 106 via, for example, a cable (not shown in FIG. 1).

The implantable component 104 comprises an implant body 114, a lead region 116, and an elongate intra-cochlear stimulating assembly 118. The implant body 114 comprises a stimulator unit 120, an internal/implantable coil 122, and an internal receiver/transceiver unit 124, sometimes referred to herein as transceiver unit 124. The transceiver unit 124 is connected to the implantable coil 122 and, generally, a magnet (not shown) fixed relative to the internal coil 122.

The magnets in the external component 102 and implantable component 104 facilitate the operational alignment of the external coil 106 with the implantable coil 122. The operational alignment of the coils enables the implantable coil 122 to transmit/receive power and data to/from the external coil 106. More specifically, in certain examples, external coil 106 transmits electrical signals (e.g., power and stimulation data) to implantable coil 122 via a radio frequency (RF) link. Implantable coil 122 is typically a wire antenna coil comprised of multiple turns of electrically insulated single-strand or multi-strand platinum or gold wire. The electrical insulation of implantable coil 122 is provided by a flexible molding (e.g., silicone molding). In use, transceiver unit 124 may be positioned in a recess of the temporal bone of the recipient. Various other types of energy transfer, such as infrared (IR), electromagnetic, capacitive and inductive transfer, may be used to transfer the power and/or data from an external device to a cochlear implant and, as such, FIG. 1 illustrates only one example arrangement.

Elongate stimulating assembly 118 is configured to be at least partially implanted in cochlea 130 and includes a plurality of longitudinally spaced intra-cochlear electrical stimulating contacts (electrodes) 128 that collectively form a contact array 126. Stimulating assembly 118 extends through an opening in the cochlea 130 (e.g., cochleostomy 132, the round window 134, etc.) and has a proximal end connected to stimulator unit 120 via lead region 116 that extends through mastoid bone 119. Lead region 116 couples the stimulating assembly 118 to implant body 114 and, more particularly, stimulator unit 120.

In general, the sound processor in sound processing unit 112 is configured to execute sound processing and coding to convert a detected sound into a coded signal that represents the detected sound signals. These encoded data are sometimes referred to herein as processed sound signals and are sent to the implantable component 104. The stimulator unit 120 is configured to utilize the processed sound signals to generate electrical stimulation signals that are delivered to the recipient's cochlea via one or more stimulation channels. In this way, cochlear implant stimulates the recipient's auditory nerve cells, bypassing absent or defective hair cells that normally transduce acoustic vibrations into neural activity.

Figure 2:
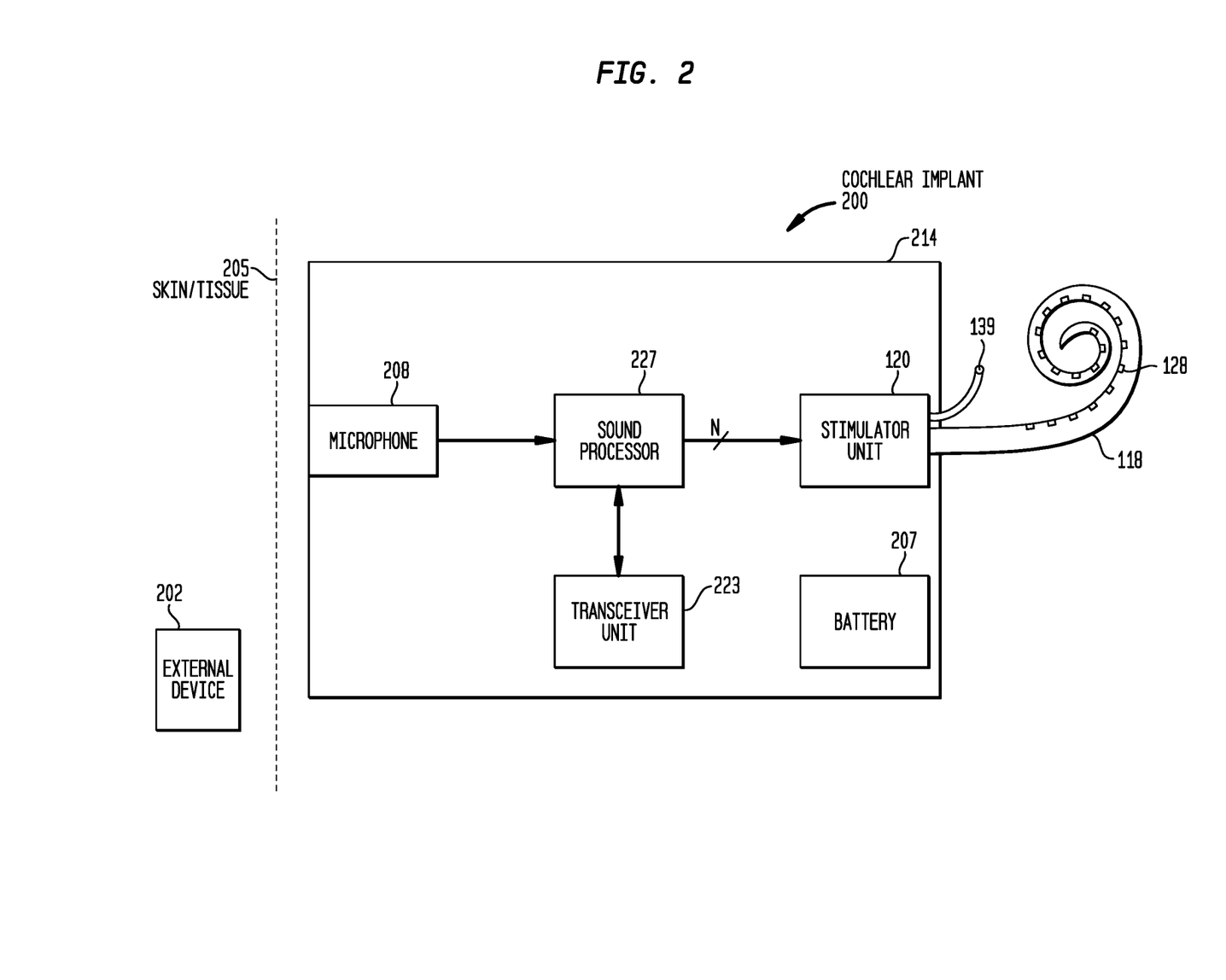
FIG. 2 is a block diagram of a totally implantable cochlear implant that may be fit to a recipient using the individualized fitting techniques presented herein.

FIG. 1 illustrates an arrangement in which the cochlear implant 100 includes an external component. However, it is to be appreciated that embodiments of the present invention may be used to fit other cochlear implants to a recipient. For example, FIG. 2 is a functional block diagram of an exemplary totally implantable cochlear implant 200 that may be fit to a recipient using the individualized fitting techniques presented herein. Since the cochlear implant 200 is totally implantable, all components of cochlear implant 200 are configured to be implanted under skin/tissue 205 of a recipient. Because all components are implantable, cochlear implant 200 operates, for at least a finite period of time, without the need of an external device. An external device 202 can be used to, for example, charge the internal power source (battery) 207. External device 202 may be a dedicated charger or a conventional cochlear implant sound processor.

Cochlear implant 200 includes an implant body (main implantable component) 214 and an implantable microphone 208, an elongate intra-cochlear stimulating assembly 118 as described above with reference to FIG. 1. The microphone 208 may be disposed in, or electrically connected to, the implant body 214. The implant body 214 further comprises an internal transceiver unit 223, one or more processors 227, a stimulator unit 120 as described with reference to FIG. 1, and the battery 207. Although FIG. 2 illustrates an example with implantable microphones 208, it is to be appreciated that the techniques presented herein may be used with devices that include external microphones.

At least one of the one or more processors 227 is configured to execute sound processing and coding to convert received/detected sound signals (e.g., received by microphone 208) into processed sound signals. The transceiver unit 223 permits cochlear implant 200 to receive and/or transmit signals to external device 202. For example, transceiver unit 223 may be configured to transcutaneously receive power and/or data from external device 202. However, as used herein, transceiver unit 223 refers to any collection of one or more implanted components which form part of a transcutaneous energy transfer system. Further, transceiver unit 223 includes any number of component(s) which receive and/or transmit data or power, such as, for example a coil for a magnetic inductive arrangement, an antenna for an alternative RF system, capacitive plates, or any other suitable arrangement.

As noted above, FIG. 1 illustrates an embodiment in which the external component 102 includes the sound processor. As such, in the illustrative arrangement of FIG. 1, processed sound signals are provided to the implanted stimulator unit 120 via the RF link between the external coil 106 and the internal coil 122. However, in the embodiment of FIG. 2, the sound processor 227 is implanted in the recipient. As such, in the embodiments of FIG. 2, the processed sound signals do not traverse the RF link, but instead are provided directly to the stimulator unit 120.

Figure 3:
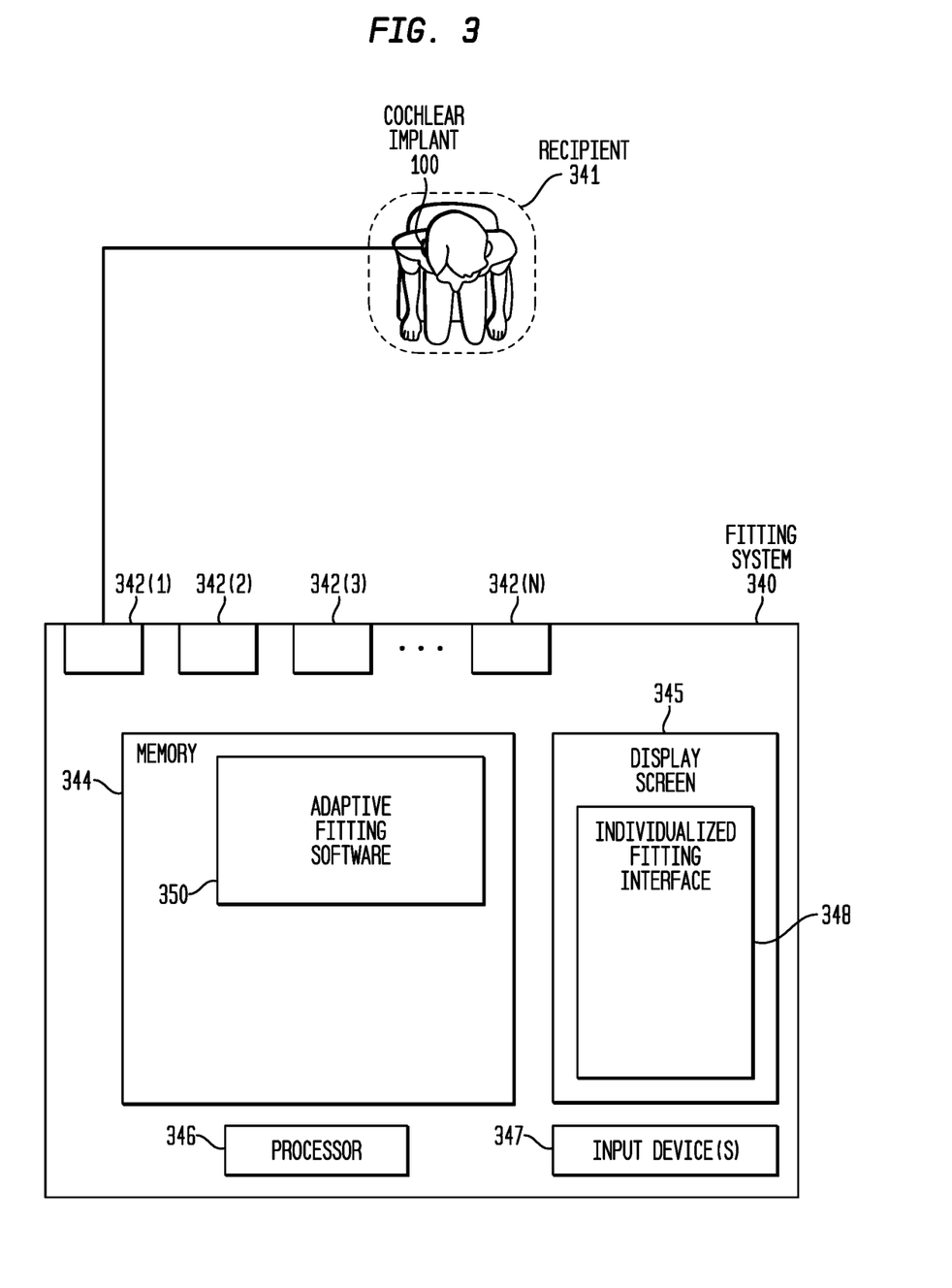
FIG. 3 is a block diagram of a fitting system, in accordance with embodiments presented herein.

As noted above, presented herein are techniques in which a fitting process is automatically individualized/customized for a specific recipient. In the individualized fitting techniques, a fitting system obtains data/information that is specific to the recipient to which the auditory prosthesis is being fitted. The fitting system is configured to analyze the recipient-specific data and to generate an individualized fitting plan/program that is specifically tailored to the attributes of the recipient. FIG. 3 is block diagram illustrating an example auditory prosthesis fitting system 340 configured to execute the individualized fitting techniques presented herein.

In the example of FIG. 3, the fitting system 340 is, in general, a computing device that comprises a plurality of interfaces/ports 342(1)-342(N), a memory 344 that includes adaptive fitting software/logic 350, a processor 346, and a display screen 345, and one or more input devices 347. The interfaces 342(1)-342(N) may comprise, for example, any combination of network ports (e.g., Ethernet ports), wireless network interfaces, Universal Serial Bus (USB) ports, Institute of Electrical and Electronics Engineers (IEEE) 1394 interfaces, PS/2 ports, etc. In the example of FIG. 3, interface 342(1) is connected to cochlear implant 100 that is at least partially implanted in a recipient 341. Interface 342(1) may be directly connected to the cochlear implant 100 or connected to an external device that is in communication with the cochlear implant (e.g., totally implantable cochlear implant 200). Interface 342(1) may be configured to communicate with cochlear implant 100 via a wired or wireless connection (e.g., telemetry, Bluetooth®, etc.). Bluetooth® is a registered trademark of Bluetooth SIG, Inc.

The display screen 345 may be, for example, a liquid crystal display (LCD) for presentation of visual information to a clinician. The one or more input devices 347 may include, for example, a keypad, keyboard, mouse, touchpad, etc. Although FIG. 3 illustrates that the display screen 345 that is separate from the one or more input devices 347, it is to be appreciated that, in certain embodiments, the display screen 345 and the one or more input devices 347 may integrated with one another (e.g., as a touchscreen).

Memory 344 may comprise read only memory (ROM), random access memory (RAM), magnetic disk storage media devices, optical storage media devices, flash memory devices, electrical, optical, or other physical/tangible memory storage devices. The processor 346 is, for example, a microprocessor or microcontroller that executes instructions for the adaptive fitting software 350. Thus, in general, the memory 344 may comprise one or more tangible (non-transitory) computer readable storage media (e.g., a memory device) encoded with software comprising computer executable instructions and when the software is executed (by the processor 346) it is operable to perform the techniques described herein.

As described further below, in accordance with the individualized fitting techniques presented herein, the adaptive fitting software 350 enables the fitting system 340 to read and process recipient-specific data (individual history of the recipient 341), such as past clinical records, previous fitting sessions logs, device usage, etc. This information may be obtained from the cochlear implant 100 itself (e.g., the sound processing unit), an auxiliary device (e.g., remote control associated with the cochlear implant), an external location (i.e., from a clinical or cloud database), etc. In addition, the adaptive fitting software 350 enables the fitting system 340 to use the recipient-specific data to automatically generate an individualized (customized) fitting plan/program for the recipient 341, exposing only the fitting functions that are clinically relevant for the recipient 341. The individualized fitting plan/program may be executed using an individualized fitting interface 348 generated and displayed at the display screen 345. As described further below, the individualized fitting interface 348 generally only includes a limited number of functional fitting modules for use in the individualized fitting process. That is, the adaptive fitting software 350 is configured to tailor the information/options displayed to the clinician to identify and enable the clinician to determine the specific settings that enable the cochlear implant 100 to operate properly for the recipient 341 being fitted.

In certain examples, only functionality that is determined to be clinically relevant to the recipient will be initially displayed and/or displayed at a top/upper level. As used herein, functionality is "clinically relevant" if the functionality is associated with one or more settings that, given the recipient's specific characteristics, enable the auditory prosthesis to convert sound signals into stimulation signals for delivery to the recipient (i.e., functions that, given the recipient-specific data, are used to determine settings that will be included in the recipient's operational map).

Figure 4:
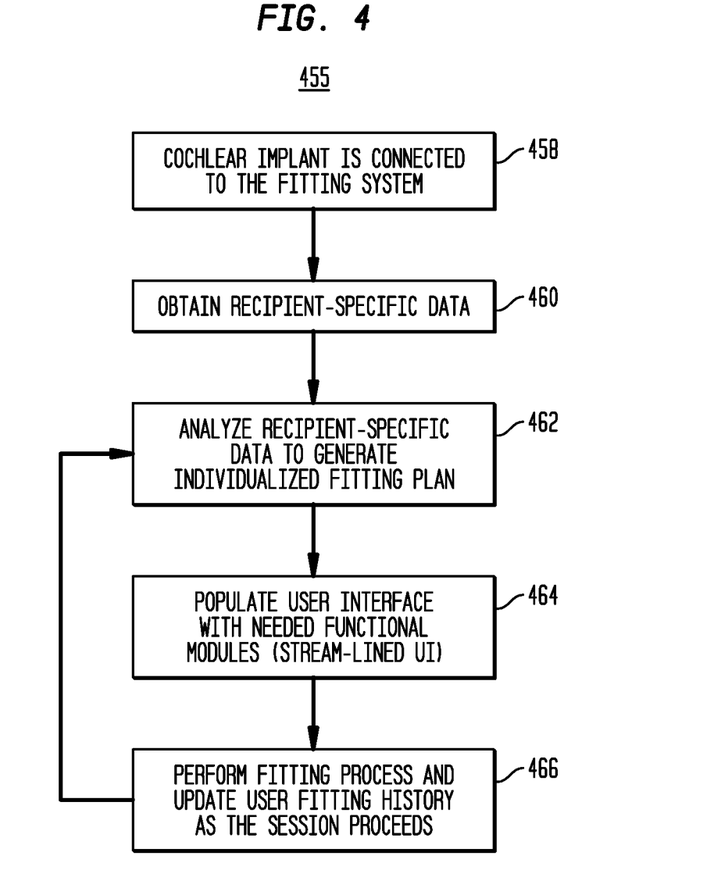
FIG. 4 is a detailed flowchart of a method, in accordance with embodiments presented herein.

FIG. 4 is a flowchart of a method 455 in accordance with the individualized fitting techniques presented herein. As noted above, the individualized fitting techniques presented herein may be used to fit different recipients to a number of different types of auditory prostheses. However, merely for ease of illustration, the method 455 of FIG. 4 will be described with reference to fitting system 340 (FIG. 3) used to fit cochlear implant 100 (FIG. 1) to a recipient 341 (FIG. 3).

Method 455 begins at 458 where the cochlear implant 100 is connected to the fitting system 340 (e.g., using interface 342(1)). At 460, the fitting system 340 obtains information/data that is specific to the recipient 341. This recipient-specific information may be any data that is associated with the particular recipient, such as the recipient's age, the recipient's hearing loss data (e.g., age of onset of hearing loss, type of hearing loss, rehabilitation state, hearing performance, etc.), past clinical records, past preferences or notes of a clinician, previous fitting sessions logs, device usage data, geographic location of the recipient, neurological data, objective measurement results (e.g., Electrode/Channel impedances, Flagged electrodes, Neural Response Telemetry, Stapedius Reflect Measurements, etc.), and/or any other clinically relevant information about the person. This recipient-specific information may be obtained from the cochlear implant 100 (i.e., the sound processing unit logs data about the user and the software could download this data and analyze it) and/or from a historical clinical database for the recipient (i.e., from a localized data store, a cloud-based data store, etc.).

At 462, the recipient-specific data is analyzed to generate an individualized fitting plan/program for the recipient that is tailored to the specific recipient (i.e., based on the recipient's age, type of hearing loss, time since implantation, historical rehabilitations, etc.). Stated differently, the adaptive fitting software 350 determines the recipient's clinically relevant settings (from the recipient data) and it then determines a plan or path (creates steps or settings) that enables the clinician to determine values for those settings for the recipient as quickly/easily as possible.

In certain examples, the adaptive fitting software 350 includes an expert system that, when executed by a processor, is configured to analyze the recipient-specific data and to generate the individualized fitting plan/program. In these examples, the expert system determines the recipient's clinically relevant settings and it then determines the plan that enables the clinician to determine values for those settings for the recipient. In other examples, the adaptive fitting software 350 includes one or more machine learning processes that, when executed, are configured to analyze the recipient-specific data and to generate the individualized fitting plan/program. In these examples, the one or more machine learning processes determine the recipient's clinically relevant settings and it then determines the plan that enables the clinician to determine values for those settings for the recipient.

The individualized fitting plan may include a list or identification of selected settings/parameters that should be determined/selected for the recipient (i.e., an indication of the parameters that, given the recipient-specific information, should be determined so as to enable proper operation of the cochlear implant 100). In certain examples, the individualized fitting plan may include a flow process that is to be executed in order to obtain values for the settings/parameters that should be determined for the recipient (e.g., a generated step-by-step process that may be followed in order to properly fit the cochlear implant to the recipient). It is to be appreciated that the individualized fitting plan may also take other forms.

At 464, the fitting system 340 is configured to provide an indication of the individualized fitting plan for the recipient. As noted above, the individualized fitting plan may include a list or identification of selected settings that should be determined for the recipient and the list or identification can be displayed at the display screen 345. Also as noted above, auditory prosthesis fitting software may include a number of different capabilities, measurements, tests, configurations, etc., that may not be needed so as to determine the selected settings for a particular recipient. As such, in accordance with certain embodiments, at 464, the fitting system 340 is configured to, at the display screen 345, populate an individualized fitting interface 348 that, at least at a top/upper level, includes only the functional fitting modules needed to determine values for the selected settings for the particular recipient. However, it is to be appreciated that the user interface 348 may be configurable by a clinician so as to add or remove different functional fitting modules, as needed.

As used herein, "functional fitting modules" refer to groups of user interface controls, such as graphical icons, buttons, scroll bars, menus, list boxes, text windows, dialog boxes, etc., that are associated with (i.e., used to perform) various functions (e.g., measurements, tests, settings, etc.). The functional fitting modules may be organized in a number of different manners. For example, the functional fitting modules may be organized by parameters that need to be measured or settings for which values are needed (e.g., modules for measurements of a recipient's threshold and comfort levels, modules for selection of a stimulation strategy, etc.), organized by the recipient's characteristics (e.g., modules for different age groups, modules for different types of hearing loss, etc.). It is to be appreciated that the various functional fitting modules available within the adaptive fitting software 350 are not necessarily pre-built and selected by the adaptive fitting software 350. Instead, in certain embodiments, the functional fitting modules may be generated in real-time (i.e., built "on-the-fly") based on the recipient-specific data. Therefore, as used herein, the "selection" of functional fitting modules refers to the selection and display of pre-built (pre-stored) functional fitting modules based on the recipient-specific information or the dynamic (real-time) generation and display of functional fitting modules based on the recipient-specific information.

Examples of functional fitting modules that may be displayed include: functional modules to measure impedances, functional modules to perform NRT measurements, functional modules to refine the recipient's operational map settings (e.g., volume, sensitivity, etc.), functional modules to adjust a bilateral balance, functional modules to measure and/or set threshold and comfort levels (e.g., per channel), functional modules to adjust front-end signal processing algorithms, functional modules to adjust applied gains, functional modules to perform adjustment of RF Power level, and other battery-life related settings, etc. These specific functional fitting modules are illustrative and, in accordance with the embodiments presented herein, different functional fitting modules, or elements/pieces thereof, may be combined together in various combinations at an individualized fitting interface.

As noted above, certain examples may make use of an expert system or machine learning processes. In such examples, the expert system or machine learning processes, when executed by a processor, are configured to select (and possibly generate) the functional modules for display as part of the user interface. That is, the functional modules could be selected, based on the determined recipient-specific data, by an expert system (pre-programmed with a specific decision matrix), or alternatively a machine-learning process/system.

Returning to FIG. 4, at 466, the fitting process is performed using the displayed functional modules so as to determine values for the selected settings for the particular recipient. As the fitting process is performed, the recipient-specific information may be updated.

In accordance with embodiments presented herein, the adaptive fitting software 350 may include all the clinical functionality available in fully-featured clinical software. However, the adaptive fitting software 350 is configured to intelligently tailor itself so as to provide an individualized fitting interface 348 that is specific for the recipient being fitted. This improves the operation of the fitting system 340 itself, as well as improves the fitting process, because the individualized fitting interface 348 only exposes functionality and settings that have between determined by the software to be clinically relevant for the individual. In other words, the adaptive fitting software 350 stream-lines the fitting process, allowing the clinician to focus on determining values for only the settings, and any associated tests/measurements, which are relevant for the specific individual being fitted. This may, for example, facilitate better outcomes, lessen the reliance on the skill of the clinician to fit the recipient leading to shorter clinical visits and enabling less experienced clinicians to properly fit auditory prostheses to recipients. The generation of an individualized fitting interface is schematically shown in FIG. 5.

Figure 5:
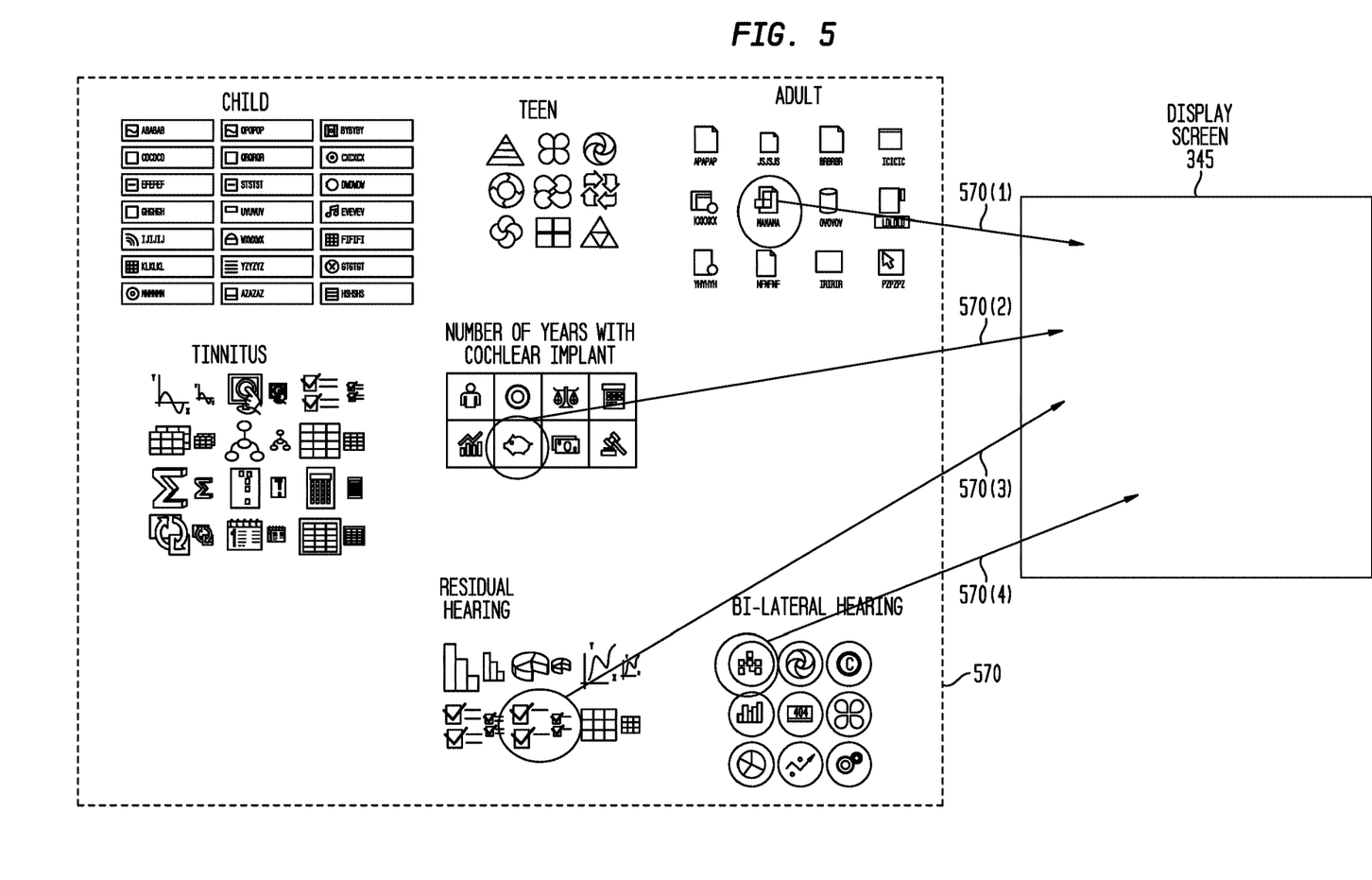
FIG. 5 is a schematic diagram illustrating the generation of an individualized fitting interface, in accordance with embodiments presented herein.

More specifically, FIG. 5 is a schematic diagram illustrating a display screen, such as display screen 345, that can be configured to display an individualized fitting interface 348 in accordance with embodiments presented herein. As noted above, depending on the analysis of the recipient-specific data, the adaptive fitting software 350 is configured to select and display different functional fitting modules which are made available as part of an individualized fitting interface. That is, different functional fitting modules can be selected from the fitting software database and populated on the fitting display screen 345.

As noted above, the functional fitting modules are groups of user interface controls, such as graphical icons, buttons, scroll bars, menus, list boxes, text windows, dialog boxes, etc., that are associated with (i.e., used to perform) various functions (e.g., measurements, tests, settings, etc.). As such, different functional fitting modules can be selected for different recipients. FIG. 5 illustrates an example in which various functional fitting modules, generally illustrated by reference number 570, are available for selection and display as part of an individualized fitting interface. The functional fitting modules 570 are generally shown as being grouped based on the recipient's characteristics, such as age group (e.g., different functional fitting modules may be selected for children, teens, and adults), number of years since receiving the cochlear implant, type of hearing loss/disability (i.e., certain functional fitting modules may be selected for recipients with residual hearing, bilateral hearing, and/or suffering from tinnitus), etc. In the example of FIG. 5, four (4) specific functional fitting modules 572(1)-572(4) are selectively activated for use as part of an individualized interface.

To facilitate understanding of the individualized fitting techniques presented herein, presented below are illustrative examples of how the adaptive fitting software 350 may operate to generate an individualized fitting plan, and associated individualized fitting interface, for different recipients. The first example illustrates how the adaptive fitting software 350 automatically configures itself for a child recipient, as opposed to an adult or teen recipient.

More specifically, in this first example, the adaptive fitting software 350 analyzes the recipient-specific information and determines that the recipient is a young child (e.g., less than 5 years old). One of the challenges in fitting a young child is that, when he/she may provide unreliable answers to subjective hearing tests (i.e., tests during which the child is asked to indicate whether or not he/she hears a sound, to identify the type of sound, evaluate a sound, etc.). As such, in accordance with embodiments presented herein, the adaptive fitting software 350 may only provide the ability to perform objective measurements, and limit/remove points that would require recipient feedback. In this example, typical settings for young child could automatically be made, including LED settings to indicate correct device function, locking of processor buttons to prevent child tampering, monitoring of headphones/wireless audio backlink to allow care giver to listen to audio in the device, enablement of own-voice detection for data logging (turn-taking metrics for language development), etc.

In contrast, a teenager recipient may be able to provide more useful subjective feedback. As such, the adaptive fitting software 350 may generate the individualized fitting interface that includes functional modules (e.g., screens, icons, functions, etc.) that require recipient feedback. In addition, processor settings and enabled functionality are those intended to make device operation and presence discreet (e.g., no LED functionality). Teenagers are also familiar with technology and the device functionality related to smart phones and wireless inter-operability can be enabled automatically. Similarly, complex device user interfaces available via buttons and remote controls/smart phones can also be enabled.

For an adult recipient, the adaptive fitting software 350 may generate the individualized fitting interface based on the past recipient clinical history and clinician preferences. For example, the adult recipient's data logs on the sound processor and/or the implant could be analyzed and the results used to determine that there are no changes in auditory or physiological performance from last session. As such, the individualized fitting interface may omit the functional modules that are used for operational map adjustments (i.e., the steps of map adjustments could be omitted from the fitting process). Alternatively, if it is determined that there are changes in the auditory or physiological performance, the fitting system could activate and display functional modules that can be used for objective measurements and/or map adjustments to allow the clinician to focus on these aspects.

In summary of this first example, there are different practices that are typically employed for fitting a child versus fitting an adult or teen recipient. In accordance with the techniques presented herein, upon connecting the recipient's auditory prosthesis, the fitting system can help the clinician to focus his/her time and attention on fitting the recipient on areas that the recipient would need the most. The fitting software would automatically configure itself to expose the parameters, algorithms, and processes as appropriate for a child (e.g., the user interface, LED settings, monitor audio stream, etc.).

Different recipients have different hearing perceptions and, in a second example, the adaptive fitting software 350 is configured based on the recipient's type of hearing perception. In particular, recipients with significant residual hearing may be implanted with an electro-acoustic hearing prostheses that is configured to deliver both electrical and acoustic stimulation to the recipient. Due to presence of residual hearing, the fitting process for a recipient implanted with an electro-acoustic hearing prosthesis is different from that of a recipient implanted with a cochlear implant. Therefore, in this illustrative example, the adaptive fitting software 350 automatically recognizes that the recipient is implanted with an electro-acoustic hearing prosthesis and, as such, activates functional modules that can perform the necessary adjustments for a recipient that has residual hearing. For example, the clinical flow may be given as: (1) measure residual hearing levels, (2) measure electrical hearing sensitivity, (3) adjust acoustic path gain levels and settings, (4) adjust electrical signal path gain levels and settings, (5) balance acoustic and electrical signal paths, and (6) determine device settings. In certain embodiments, the functional modules needed to perform each of these steps can be enabled/exposed to the clinician (via the individualized fitting interface) in sequence so as to provide the clinician with an easy to follow step-by-step process. In certain examples, the clinical flow can be further tailored/stream-lined based on, for example, past history, individual characteristics, device usage, objective measurement results, etc.

In a third example, upon analysis of the recipient-specific information, the adaptive fitting software 350 determines that the recipient suffers from tinnitus, which should be addressed during the fitting process. In this example, the adaptive fitting software 350 automatically activates tinnitus suppression modules for display as part of the individualized fitting interface. The tinnitus suppression modules may only be exposed for a recipient that has known tinnitus, or tinnitus discovered during the fitting process (i.e., tinnitus is only relevant for a proportion of recipients). In a further case, the adaptive fitting software 350 may only expose the tinnitus suppression modules when there is a problem. For example, if the adaptive fitting software 350 determines that the recipient suffers from tinnitus, but also determines that the current tinnitus settings have been successful in alleviating the tinnitus symptoms. In such circumstances, the adaptive fitting software 350 may elect to omit the tinnitus suppression modules from the individualized fitting interface (i.e., the tinnitus suppression can be by-passed or streamlined).

Neural Response Telemetry (NRT) measurements are often an important measure of physiological performance for newer cochlear implant recipients, but may be less important for more experienced recipients (i.e. who have had a cochlear implant for an extended period of time). Therefore, in a fourth example, the adaptive fitting software 350 is configured to automatically remove NRT modules from the clinical flow once the levels have stabilized. Alternatively, if another objective measure indicates a physiological change, then the NRT modules could be activated and/or other forms of clinical measurement modules may be exposed/suggested based on clinical history, device usage, etc. These measurement modules may include, for example, impedance measurement modules, electro-cochleography modules, stapedius reflex measurement modules, audiogram modules, speech perception test modules, speech in noise test modules, localization test modules, etc. By automatically selecting and activating the measurement modules that are needed by a particular recipient, the adaptive fitting software 350 removes the need for the clinician to wade through various options and/or manually determine which is appropriate. This ensure that the needed functionality is available that can maximize clinical outcomes in the most efficient manner.

As the recipient ages, certain settings may need more attention than others. Therefore, in a fifth example in which an aging recipient is undergoing a fitting process, the adaptive fitting software 350 may determine the device usage logs, or previous clinical data (perhaps including logs from earlier devices), that certain settings are very important/heavily used by the specific individual. As such, the functional modules related to these settings are automatically activated and displayed at the individualized fitting interface. Similarly, the adaptive fitting software 350 may determine which functions/settings are unused by the recipient and, accordingly, automatically disable the functional modules related to these unused settings. For example, the data logs may indicate that the recipient is regularly exposed to wind noise and automatically suggest that the functional module for evaluating the Wind Noise Reduction settings is enabled and included in the individualized fitting interface.

In a sixth example, the recipient's geographic location could be used to expose/hide functional modules. For instances, the geographic location could be used to expose/hide functional modules related to settings that are/are not regulatory approved in a particular country. In addition, the recipient's geographic location could be used to expose/hide functional modules that are catered to environmental conditions in the particular region (e.g., for a recipient in a more humid climate, the software could expose/perform device integrity tests on the microphones, coils, or other functionality that could be affected by the humidity).

In another example, the device usage data could indicate that the recipient is exposed to certain type(s) of environmental noise, and thereby the adaptive fitting software 350 may then expose an appropriate noise canceller or signal processing algorithm at the user interface. In a similar example, the adaptive fitting software 350 may determine that a specific signal processing algorithm is being used by the specific recipient, but that the recipient's data logs indicate that the settings of the algorithm are sub-optimal (i.e., failing to provide the recipient with the intended to maximum benefit). In these examples, the adaptive fitting software 350 could then expose the specific signal processing algorithm at the user interface and, for example, suggest a preferred configuration/parameter setting for the algorithm in question, illustrate example tests for optimizing the algorithm settings, etc.

In a further example, the adaptive fitting software 350 could automatically adapt to the clinician as well as the recipient. For example, if a clinician prefers certain types of listening tests or objective measures the system would automatically expose them and push the rarely used features to a less prominent place in the user interface flow.

As noted, the above examples are illustrative and have been provided to facilitate understanding of the individualized fitting techniques presented herein. It is to be appreciated that these examples are not mutually exclusive and that the adaptive fitting software may use any of a number of different pieces of recipient-specific information to generate an individualized fitting interface.

The individualized fitting techniques presented herein have been primarily described above with reference to use of the individualized fitting techniques in a clinical setting/arrangement where the fitting process is controlled by a clinician. However, it is to be appreciated that the use of the individualized fitting techniques in a clinical setting is illustrative and that the individualized fitting techniques presented herein may be used in remote-care or recipient-directed fitting arrangements. That is, because the adaptive fitting software is able to analyze the recipient-specific information and automatically generate an individualized fitting plan and/or interface, the individualized fitting techniques may also be used by a recipient, caregiver, or other user outside of a clinic to perform certain measurements and/or set, evaluate, adjust, etc., one or more settings of an auditory prosthesis.

Figure 6:
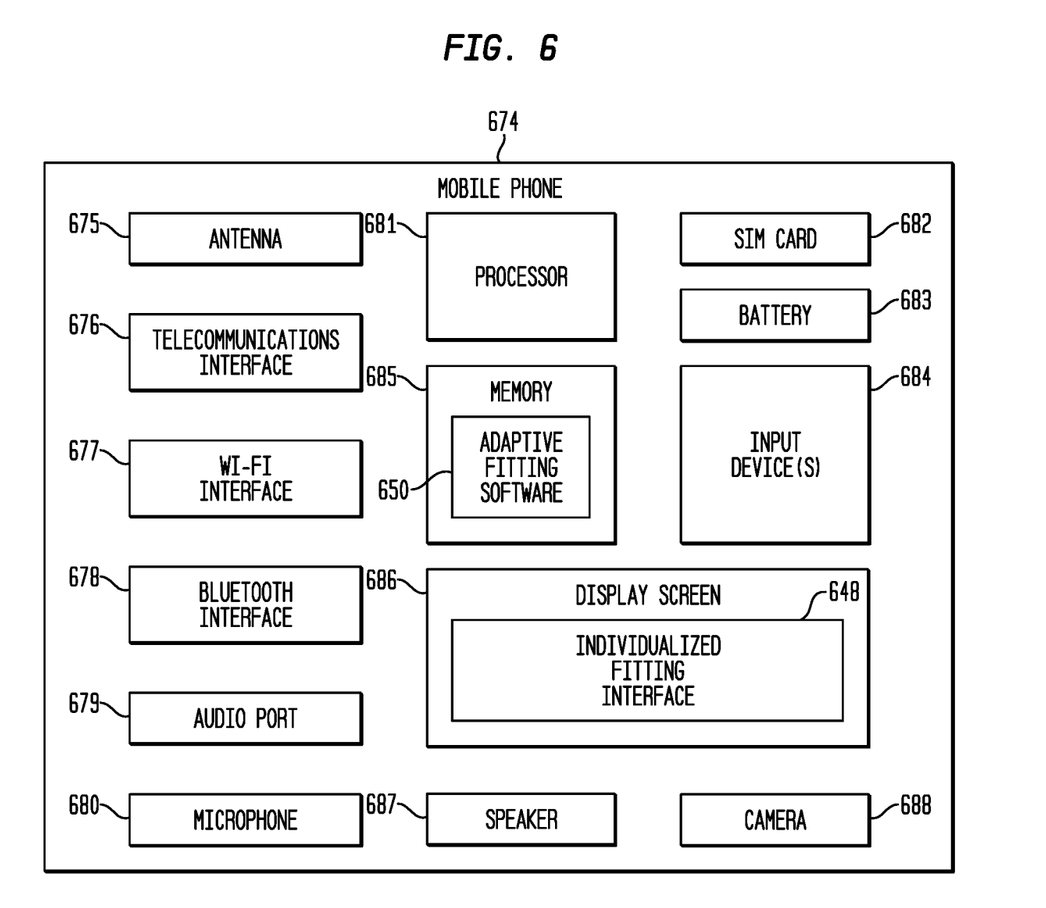
FIG. 6 is a block diagram of a mobile device configured to perform individualized fitting techniques, in accordance with embodiments presented herein.

FIG. 6 is a block diagram of an illustrative arrangement for another auditory prosthesis fitting system in the form of a mobile device 674 that is configured to perform individualized fitting techniques. It is to be appreciated that FIG. 6 is merely illustrative and that the individualized fitting techniques may be performed at other devices having different arrangements than that shown in FIG. 6.

In the example of FIG. 6, the mobile device 674 is a mobile phone that comprises an antenna 675 and a telecommunications interface 676 that are configured for communication on a wireless communication network for telephony services (e.g., a Global System for Mobile Communications (GSM) network, code division multiple access (CDMA) network, time division multiple access (TDMA), or other kinds of networks). Mobile phone 674 also includes a wireless local area network interface 677 and an infrared (IR) or Bluetooth® interface 678. The Bluetooth® trademark is owned by the Bluetooth® SIG. The wireless local area network interface 677 allows the mobile phone 674 to exchange data or connect to the Internet using, for example, 2.4 Gigahertz (GHz) Ultra high frequency (UHF) and/or 5 GHz Super high frequency (SHF) radio waves. The Bluetooth® interface 678 enables the mobile phone 674 to wirelessly communicate (i.e., directly receive and transmit data to/from another device via a wireless connection). In certain examples, the Bluetooth® interface 678 may be used to wirelessly connect the mobile phone 674 to the cochlear implant 100 (FIG. 1). It is to be appreciated that the use of a wireless local area network interface in combination with a Bluetooth® interface is merely illustrative and that any other interfaces now known or later developed including, but not limited to, Institute of Electrical and Electronics Engineers (IEEE) 802.11, IEEE 802.16 (WiMAX), fixed line, Long Term Evolution (LTE), etc. interfaces may also or alternatively form part of the mobile phone 674.

Mobile phone 674 also comprises an audio port 679, one or more sound input elements, such as a microphone 680, a speaker 687, a camera 688, a display screen 686, one or more input devices 684, a subscriber identity module or subscriber identification module (SIM) card 682, a battery 683, a processor 681, and a memory 685. The display screen 686 may be, for example, a liquid crystal display (LCD) for presentation of visual information to a user. The one or more input devices 347 may include, for example, a keypad, touchpad, etc. Although FIG. 6 illustrates that the display screen 686 that is separate from the one or more input devices 684, it is to be appreciated that, in certain embodiments, the display screen 686 and the one or more input devices 684 may integrated with one another (e.g., as a touchscreen).

Memory 685, which includes adaptive fitting software 650, may comprise ROM, RAM, magnetic disk storage media devices, optical storage media devices, flash memory devices, electrical, optical, or other physical/tangible memory storage devices. The processor 681 is, for example, a microprocessor or microcontroller that executes instructions for the adaptive fitting software 650. Thus, in general, the memory 685 may comprise one or more tangible (non-transitory) computer readable storage media (e.g., a memory device) encoded with software comprising computer executable instructions and when the software is executed (by the processor 681) it is operable to perform individualized fitting techniques described herein.

Similar to the clinical arrangements, the adaptive fitting software 650 enables the mobile phone 674 to read and process recipient-specific data (individual history of a recipient), such as past clinical records, previous fitting sessions logs, device usage, etc. This information may be obtained from an auditory prosthesis, a remote control associated with the prosthesis, a data store in the mobile phone 674, an external location (i.e. from a clinical or cloud database), etc. In addition, the adaptive fitting software 650 enables the mobile phone 674 to use this recipient-specific data to automatically generate an individualized (customized) fitting plan/program for the recipient, exposing only the fitting functions that are clinically relevant for the recipient. The individualized fitting plan/program may be executed using an individualized fitting interface 648 generated and displayed at the display screen 686. Similar to the above clinical embodiments, the individualized fitting interface 648 generally only includes a limited number of functional fitting modules for use in the individualized fitting process. That is, the adaptive fitting software 650 is configured to tailor the information/options displayed at the display screen 686 for the specific needs of the recipient being fitted. In certain examples, only functionality that is determined to be clinically relevant to the recipient will be initially displayed and/or displayed at a top/upper level.

Generally speaking, due in part to health/safety issues, a recipient is provided with a limited ability to initiate changes to his/her device. As such, the adaptive fitting software 650 may only provide a user with a subset of the functionality that can be provided to a clinician (i.e. may only be able to active specific functional modules for inclusion as part of the individualized fitting interface 648). For example, the individualized fitting interface 648 may only allow the recipient to change a limited number of stimulation parameters, such as a recipient's threshold or comfort levels, which may be changed without approval of a clinician or audiologist. In certain examples, any settings/parameters selected by a user at the mobile phone 676 may be uploaded to a database for evaluation and approval by a clinician or audiologist and, if approved, provided to the cochlear implant for instantiation. In another embodiment, the individualized fitting process may be remotely monitored by a clinician or audiologist for real-time re-programming and/or guidance.

Figure 7:
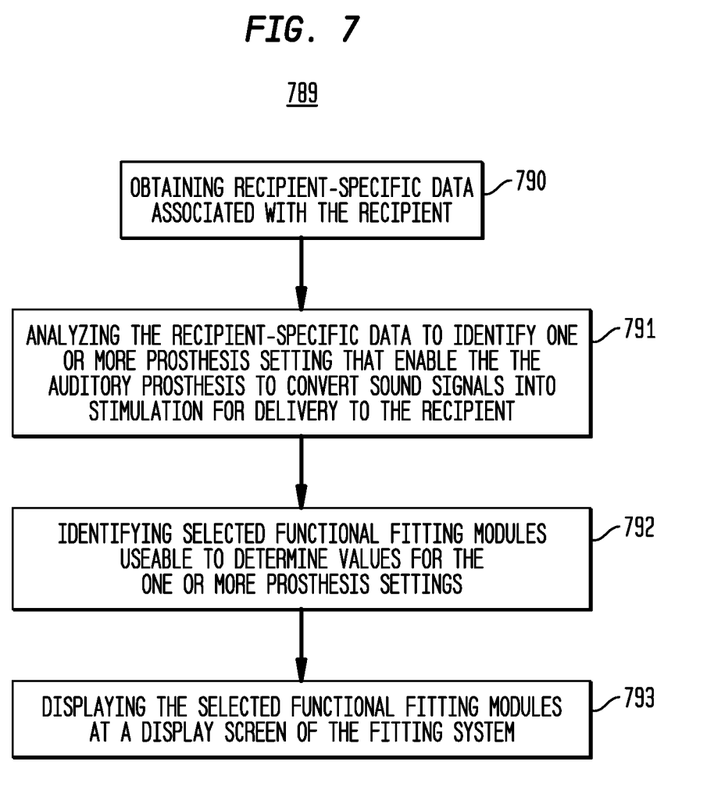
FIG. 7 is a high-level flowchart of a method, in accordance with embodiments presented herein.

FIG. 7 is a flowchart of a method 790 for fitting an auditory prosthesis to a recipient with a fitting system, in accordance with embodiments presented herein. Method 789 begins at 790 where the fitting system obtains recipient-specific data associated with the recipient. At 791, the fitting system analyzes the recipient-specific data to identify one or more prosthesis setting that enable the auditory prosthesis to convert sound signals into stimulation signals for delivery to the recipient. At 792, the fitting system identifies selected functional fitting modules useable to determine values for the one or more prosthesis settings. At 793, the fitting system displays the selected functional fitting modules at a display screen of the fitting system.

Figure 8:
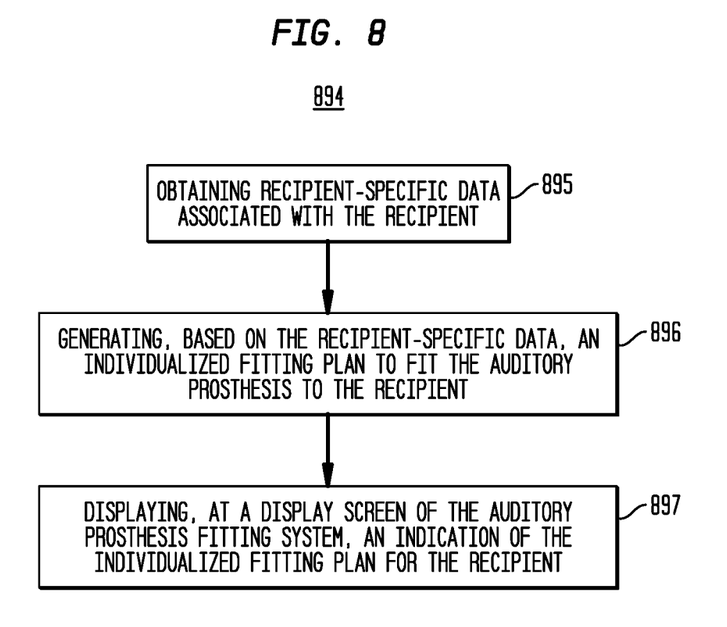
FIG. 8 is a high-level flowchart of another method, in accordance with embodiments presented herein.

FIG. 8 is a flowchart of a method 894 for fitting an auditory prosthesis to a recipient with an auditory prosthesis fitting system, in accordance with embodiments presented herein. Method 894 begins at 895 where the auditory prosthesis fitting system obtains recipient-specific data associated with the recipient. At 896, the auditory prosthesis fitting system generates, based on the recipient-specific data, an individualized fitting plan to fit the auditory prosthesis to the recipient. At 897, the auditory prosthesis fitting system displays, at a display screen of the auditory prosthesis fitting system, an indication of the individualized fitting plan for the recipient.

As detailed, prepared herein are techniques in which a device, which has a wide variety of clinical functionality available, is configured to intelligently tailor itself, and its user interface, for a specific individual being fitted (i.e., only expose functionality and settings that is clinically relevant for the individual). As noted above, the techniques presented herein may create a suggested flow (steps) for the clinician to execute on the recipient, or could limit the types of measurements that could be performed. As a result, the techniques presented herein can save time and ease clinical burden (i.e., minimize the guesswork required by clinicians, especially non-experienced clinicians). This may bring more comfort and create less stress for clinicians who are not experienced with the fitting software and allow recipients to get the most benefits in the limited time available from the clinician. That is, the techniques presented herein may enable clinicians to only spend time on areas that are most clinically relevant (i.e., the settings that are most required by a recipient).

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An apparatus for fitting an auditory prosthesis to a recipient, comprising:
   a display screen;
   one or more user input devices; and
   one or more processors configured to:
      obtain recipient-specific data associated with the recipient of the auditory prosthesis;
      analyze the recipient-specific data with a machine learning process to determine a first set of auditory prosthesis settings that are clinically relevant for the recipient, wherein the first set of auditory prosthesis settings comprise only a subset of a plurality of auditory prosthesis settings that may be determined for the auditory prosthesis; and
      based on the recipient-specific data, automatically generate and display an individualized fitting interface at the display screen that exposes to a user only a first set of functional fitting modules that are useable to determine the first set of auditory prosthesis settings that are clinically relevant for the recipient.

2. The apparatus of claim 1, wherein to analyze the recipient-specific data with a machine learning process to determine a first set of auditory prosthesis settings that are clinically relevant for the recipient, the one or more processors are configured to:
   analyze only the recipient-specific data to determine the first set of auditory prosthesis settings, wherein the first set of auditory prosthesis settings comprise setting that enable the auditory prosthesis to convert sound signals into stimulation signals for delivery to the recipient.

3. The apparatus of claim 1, wherein the one or more processors are configured to:
   generate, in real-time, the first set of functional fitting modules based on the recipient-specific data.

4. The apparatus of claim 1, wherein the one or more processors are configured to:
   select the first set of functional fitting modules from a plurality of pre-built functional fitting modules.

5. The apparatus of claim 1, wherein the recipient-specific data associated with the recipient of the auditory prosthesis is obtained from the auditory prosthesis.

6. The apparatus of claim 1, wherein the recipient-specific data associated with the recipient of the auditory prosthesis is obtained from a clinical database.

7. The apparatus of claim 1, wherein the recipient-specific data comprises at least one of an age of the recipient, a type of hearing loss experienced by the recipient, or an age of onset of hearing loss.

8. The apparatus of claim 1, wherein the apparatus is a mobile device.

9. A method for fitting an auditory prosthesis to a recipient with a fitting system, wherein the fitting system is configured to enable a clinician to set a plurality of settings for the auditory prosthesis, the method comprising:
   obtaining recipient-specific data associated with the recipient;
   analyzing the recipient-specific data with a machine learning process to identify first set of prosthesis settings that enable the auditory prosthesis to convert sound signals into stimulation signals for delivery to the recipient, wherein the first set of prosthesis settings comprising only a subset of the plurality of settings that may be set by the fitting system;
   identifying selected functional fitting modules useable to determine values for the first set of prosthesis settings, wherein the selected functional fitting modules comprise only a subset of a plurality of functional fitting modules available at the fitting system; and
   displaying only the selected functional fitting modules at a display screen of the fitting system.

10. The method of claim 9, wherein identifying, the selected functional fitting modules comprises:
    generating, in real-time, each of the selected functional fitting modules useable to determine values for the first set of prosthesis settings.

11. The method of claim 9, wherein the plurality of functional fitting modules comprise a plurality of pre-stored functional fitting modules stored in the fitting system and wherein identifying, the selected functional fitting modules comprises:
    selecting each of the selected functional fitting modules from the plurality of pre-stored functional fitting modules.

12. The method of claim 9, wherein obtaining recipient-specific data associated with the recipient comprises:
    obtaining recipient-specific data from the auditory prosthesis.

13. The method of claim 9, wherein obtaining recipient-specific data associated with the recipient comprises:
    obtaining recipient-specific data from a clinical database.

14. The method of claim 9, wherein the recipient-specific data comprises at least one of an age of the recipient, a type of hearing loss experienced by the recipient, or an age of onset of hearing loss.

15. A method for fitting an auditory prosthesis to a recipient, comprising:
    at an auditory prosthesis fitting system:
       obtaining recipient-specific data associated with the recipient;
       analyzing the recipient-specific data with a machine learning process to determine a first set of auditory prosthesis settings that are clinically relevant for the recipient, wherein the first set of auditory prosthesis settings comprise only a subset of a plurality of auditory prosthesis settings that may be determined for the auditory prosthesis;
       generating an individualized fitting plan to determine values for each of the settings in the first set of auditory prosthesis settings; and displaying, at a display screen of the auditory prosthesis fitting system, an indication of the individualized fitting plan for the recipient.

16. The method of claim 15, wherein the auditory prosthesis fitting system is configurable for use in determining a plurality of auditory prosthesis settings, and wherein displaying the indication of the individualized fitting plan for the recipient comprises:

displaying, at the display screen, an individualized fitting interface that includes only a first set of functional fitting modules needed to determine values for each of the settings in the first set of auditory prosthesis settings, wherein the first set of functional fitting modules comprise only a subset of a plurality of functional fitting modules available at the auditory prosthesis fitting system.

17. The method of claim 16, furthering comprising:

generating the functional fitting modules in real-time based on the recipient-specific data.

18. The method of claim 15, wherein obtaining recipient-specific data associated with the recipient comprises:

obtaining recipient-specific data from the auditory prosthesis.

19. The method of claim 15, wherein obtaining recipient-specific data associated with the recipient comprises:

obtaining recipient-specific data from a clinical database.

20. The method of claim 15, wherein obtaining recipient-specific data associated with the recipient comprises:

obtaining at least one of an age of the recipient, a type of hearing loss experienced by the recipient, or an age of onset of hearing loss.

21. The method of claim 15, wherein obtaining recipient-specific data associated with the recipient comprises:

obtaining at least one past clinical record associated with the recipient.

22. The method of claim 15, wherein the auditory prosthesis is a cochlear implant, and wherein generating an individualized fitting plan comprises:

generating a cochlear implant fitting plan that is specifically tailored to the recipient.

* * * * *